United States Patent [19]

Godtfredsen

[11] Patent Number: 5,292,727
[45] Date of Patent: Mar. 8, 1994

[54] USE OF THE TREATMENT OF ACNE

[75] Inventor: Wagn Ole Godtfredsen, Vaerlose, Denmark

[73] Assignee: Leo Pharmaceutical Products Ltd., Ballerup, Denmark

[21] Appl. No.: 859,529
[22] PCT Filed: Feb. 25, 1991
[86] PCT No.: PCT/DK91/00056
§ 371 Date: Jun. 11, 1992
§ 102(e) Date: Jun. 11, 1992
[87] PCT Pub. No.: WO91/12807
PCT Pub. Date: Sep. 5, 1991

[30] Foreign Application Priority Data

Mar. 1, 1990 [GB] United Kingdom ............... 9004544

[51] Int. Cl.$^5$ ........................... A61K 31/595
[52] U.S. Cl. ................... 514/168; 514/171; 514/859; 552/653
[58] Field of Search ............. 552/653, 167, 653; 514/171, 859

[56] References Cited

U.S. PATENT DOCUMENTS 5,104,864 4/1982 DeLuca .................. 514/167
5,145,846 9/1992 Baggiolini et al. .......... 514/167

FOREIGN PATENT DOCUMENTS 129003 12/1984 European Pat. Off.
215956 4/1987 European Pat. Off.
398217 11/1990 European Pat. Off.

OTHER PUBLICATIONS

Abstract of WO 87/00834 (1987).
Calverley, M., Tetrahedron, 43:4609–4619 (1987).
Binderup, L. and Bramm, E., Biochemical Pharmacology, 37:889–895 (1988).
Ostrem, V. K. et al. Proc. Natl. Acad. Sci. USA, 84:2610–2614 (1987).
Abe, J. et al. FEBS Letters, 226:58–62 (1987).
Ikekawa, N. et al. Chem. Pharm. Bull., 35:4362–4365 (1987).
Murdoch et al., "Calcipotriol", Drugs, 43(3):415–429 (1992).
Kragballe, Arch. Dermatol. Res., 284(Supp):S:30–36 (1992).
Chatelus et al., Pharmacol. Skin Basel Karger, 3:144–148 (1989).
Bouclier et al., Skin Pharmacol., 4:65–73 (1991).
Binderup et al., Biochemical Pharmacology, 42(8):1569–1575 (1991).
Chemical Abstracts, vol. 112, No. 10, Mar. 5, 1990, p. 446.
Chemical Abstracts, vol. 109, Jul. 4–25, 1988, pp. 391.
Schwetz, Rundschau Med. (PRAXIS), vol. 69, No. 7., 1980, A. Lassus: "Die Nachbehandlung Der Akne", pp. 225–227.

Primary Examiner—Frederick E. Waddell
Assistant Examiner—T. J. Criares
Attorney, Agent, or Firm—Cushman, Darby & Cushman

[57] ABSTRACT

The present invention relates to the use of certain vitamin D analogues in the preparation of a pharmaceutical preparation for the treatment of acne. The preparation contains a vitamin D analogue (calcipotriol) which has only moderate activity on the calcium metabolism when compared to 1,25-(OH)$_2$ D$_3$, but has retained the ability to activate receptors for 1,25-(OH)$_2$ D$_3$ not associated with calcium absorption or bone calcium mobilization.

2 Claims, No Drawings

USE OF THE TREATMENT OF ACNE

This invention relates to the use of certain Vitamin D analogues in the preparation of a pharmaceutical preparation for the treatment of acne.

Among the factors contributing to the aetiology of acne, an increased sebum production appears to be of major importance, as the severity of the acne parallels sebum excretion rates.

In accordance with this, the reduction of sebum production induced by treatment with oestrogens or isotretinoin leads to an improvement in acne. However, the hormonal effects of the former precludes its widespread use, and isotretinoin is teratogenic and is only used for very severe acne due to this and other side effects (Drug and Therapeutics Bulletin, Vol. 22, No. 24, Dec. 3, 1984).

Recently it has been found that topical application of $1\alpha$, 25-dihydroxyvitamin $D_3$ ($1\alpha$, 25-$(OH)_2D_3$) reduces the size of sebaceous glands in the ear of male Syrian hamsters (V. L. Malloy et al, The tricontinental Meeting for Investigative Dermatology, Washington, USA, 1989).

However, this observation may be of limited utility in the human medicine because transdermal absorption after topical application of $1\alpha$, 25-$(OH)_2D_3$ or systemic treatment with this compound, may, due to its potent calcemic activity, give rise to undesired effects leading to hypercalcemia.

However, by choosing a vitamin D analogue which has only moderate activity on calcium metabolism compared to 1,25-$(OH)_2D_3$, but having retained the ability to activate receptors for 1,25-$(OH)_2D_3$ not associated with calcium absorption or bone calcium mobilization it is possible to treat acne successfully without having the risk of inducing hypercalcemia.

Examples of such vitamin D analogues for use in the present pharmaceutical preparations are 1) compounds described in international patent application No. PCT/DK86/00081, international filing date 14th Jul., 1986, International Publication No. WO 87/00834, in particular the compound designated MC 903 (example 5 in said patent application) (confer also Calverley, M., Tetrahedron 43, 4609–4619 (1987); Binderup, L. and Bramm, E., Biochemical Pharmacology 37, 889–895 (1988)), 2) compounds described in international patent application No. PCT/DK89/00079, international filing date 7th Apr., 1989, in particular Compound 35 (Example 2), Compound 37 (Example 4), Compound 38 (Example 5), Compound 54 (Example 9), Compound 55 (Example 10), and Compound 59 (Example 12)

3) 24-homo- and 26-homo-1,$\alpha$25-dihydroxyvitamin $D_3$ (together with their 22,23-didehydro-analogues) (Ostrem, V. K. et al, Proc. Natl. Acad. Sci. USA 84, 2610–2614 (1987)), 4) 20-oxa-21-nor-1$\alpha$,25-dihydroxyvitamin $D_3$ and 22-oxa-1$\alpha$,25-dihydroxyvitamin $D_3$ (Abe, J. et al, FEBS Letters 226, 58–62 (1987)), and 5) 26,27-dimethyl- and 26,27-diethyl-1$\alpha$,25-dihydroxyvitamin $D_3$, and 24,24-difluoro-24-homo-1$\alpha$,2-5dihydroxyvitamin $D_3$ (Ikekawa, N. et al, Chem. Pharm. Bull. 35, 4362–65 (1987)), The mentioned compounds shall form part of pharmaceutical preparations, in particular for topical use, which are useful in the treatment of human disorders as described above, such as a liniment, a lotion or a cream which in addition to the vitamin D analogues in question may contain further active ingredients. The concentration of the active ingredients will depend upon the choice of vitamin D analogues but will generally be between 1 and 100 $\mu g/g$.

The formulations will be applied once or twice daily for prolonged periods of time.

The formulations prepared according to the present invention comprise an active compound in association with a pharmaceutically acceptable carrier therefore and optionally other therapeutic ingredient(s). The carrier(s) must be "acceptable" in the sense of being compatible with the other ingredients of the preparations and not deleterious to the recipient thereof.

The preparations may conveniently be prepared by any of the methods well known in the art of pharmacy. All methods include the step of bringing the active compound into association with the carrier which constitutes one or more accessory ingredients. In general, the preparations are prepared by uniformly and intimately bringing the active compound into association with a liquid carrier or a finely divided solid carrier or both, and then, if necessary, shaping the product into the desired preparation.

Preparations suitable for topical administration include liquid or semi-liquid preparations such as liniments, lotions, applicants, oil-in-water or water-in-oil emulsions such as creams, ointments or pastes; or solutions or suspensions such as drops.

In addition to the aforementioned ingredients, the preparations of this invention may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

The preparations may, as mentioned above, contain further therapeutically active compounds usually applied in the above mentioned treatment.

In the topical treatment, ointments, creams, or lotions containing from 1–100 $\mu g/g$ of the vitamin D analogues or metabolites are administered.

Preparations of the present invention suitable for oral administration may be in the form of discrete units as capsules, sachets, tablets or lozenges, each containing a predetermined amount of the active compound; in the form of a powder or granules; in the form of a solution or a suspension in an aqueous liquid or non-aqueous liquid; or in the form of an oil-in-water emulsion or a water-in-oil emulsion. The active compound may also be administered in the form of a bolus, electuary or paste.

A tablet may be made by compressing or moulding the active compound optionally with one or more accessory ingredients. Compressed tablets may be prepared by compressing, in a suitable machine, the active compound in a free flowing form such as a powder or granules, optionally mixed by a binder, lubricant, inert diluent, surface active or dispersing agent. Moulded tablets may be made by moulding, in a suitable machine, a mixture of the powdered active compound and suitable carrier moistened with an inert liquid diluent.

Preparations for rectal administration may be in the form of a suppository incorporating the active compound and a carrier such as cocoa butter, or in the form of an enema.

Preparations suitable for parenteral administration conveniently comprise a sterile oily or aqueous preparation of the active compound which is preferably isotonic with the blood of the recipient.

In addition to the aforementioned ingredients, the preparations of this invention may include one or more additional ingredients such as diluents, buffers, flavouring agents, binders, surface active agents, thickeners, lubricants, preservatives, e.g. methyl hydroxybenzoate (including anti-oxidants). emulsifying agents and the like.

The oral preparations are formulated, preferably as tablets, capsules, or drops, containing from 0.5–1000 μg of the vitamin D analogues or metabolites, per dosage unit.

The present invention further concerns a method for treating patients suffering from acne, said method consisting of administering topically to a patient in need of treatment an effective amount of one or more of the above mentioned vitamin D analogues or metabolites, alone or in combination with one or more other therapeutically active compounds usually applied in such treatment. The treatment with the present compounds concomitantly with further therapeutically active compounds may be simultaneous or with intervals.

The invention will now be further described in the following non-limiting Examples:

EXAMPLE 1

Cream Containing MC 903

In 1 g almond oil was dissolved 1 mg MC 903. To this solution was added 40 g of mineral oil and 20 g of self-emulsifying beeswax. The mixture was heated to liquify. After the addition of 40 ml hot water, the mixture was mixed well. The resulting cream contains approximately 10 μg of MC 903 per gram of cream.

EXAMPLE 2

Cream containing 22-oxa-1α,25-dihydroxy vitamin $D_3$

By using the procedure described in Example 1, but replacing MC 903 with 22-oxa-1α,25-dihydroxyvitamin $D_3$, the desired cream was obtained.

EXAMPLE 3

Cream containing 50 μg MC 903/g

| MC903 | 50 mg |
|---|---|
| Cetomacrogol 1000 | 25 g |
| Cetostearyl alcohol | 75 g |
| Chloroallylhexaminium chloride | 0.5 g |
| Glycerol | 30 g |
| Disodium hydrogenphosphate | 2 g |
| Sodium dihydrogenphosphate | 0.1 g |
| Liquid paraffin | 60 g |
| Polyoxyethylene stearylether | 12 g |
| White petrolatum | 160 g |
| Purified water up to | 1000 g |

Dissolve MC903 in a solution of glycerol, disodium hydrogenphosphate, sodium dihydrogenphosphate and polyoxyethylene stearylether dissolved in water. Mix with the melted cetomacrogol 1000, liquid paraffin, cetostearyl alcohol and white petrolatum. Homogenize the emulsion and cool. Dissolve chloroallylhexaminium chloride in part of the water and mix until homogeneous with the emulsion. Fill the cream in aluminium tubes.

EXAMPLE 4

Cream containing 100 μg MC 903/g

| MC903 | 100 mg |
|---|---|
| Cetomacrogol 1000 | 30 g |
| Cetostearyl alcohol | 60 g |
| Chloroallylhexaminium chloride | 0.5 g |
| Propylenglycol | 30 g |
| Disodium hydrogenphosphate | 2 g |
| Sodium dihydrogenphosphate | 0.1 g |
| Liquid paraffin | 50 g |
| White petrolatum | 170 g |
| Purified water up to | 1000 g |

Melt cetomacrogol 1000, cetostearyl alcohol, liquid paraffin and white petrolatum at 75° C. Dissolve propylenglycol in water at 75° C. and mix the solution with the fatty phase. Homogenize the emulsion and cool to 30° C. Mill MC903 to particle size below 5 μm and suspend in an aqueous solution of disodium hydrogenphosphate, sodium dihydrogenphosphate and chloroallylhexaminium chloride. Add the suspension to the emulsion and fill the cream in tubes.

EXAMPLE 5

Lotion containing 50 μg MC 903/g

| MC903 | 50 mg |
|---|---|
| Absolute alcohol | 400 g |
| Hydroxypropylcellulose | 1 g |
| Menthol | 1 g |
| Sodium citrate | 1 g |
| Propylenglycol | 40 g |
| Purified water up to | 1000 ml |

Dissolve hydroxypropylcellulose, sodium citrate and propylenglycol in water. Mix with a solution of MC903 and menthol in absolute alcohol. Fill the lotion in polyethylen plastic bottles.

EXAMPLE 6

Capsules containing 22-oxa-1α,25-dihydroxyvitamin $D_3$ 22-oxa-1α,25-dihydroxyvitamin $D_3$ ('22-oxa') was suspended in arachis oil to a final concentration of 5 μg '22-oxa'/ml oil. 10 Parts by weight of gelatine 5 parts by weight of glycerine, 0.08 parts by weight potassium sorbate, and 14 parts by weight distilled water were mixed together with heating and formed into soft gelatine capsules. These were then filled each with 100 μl of the '22-oxa' in oil suspension, such that each capsule contained 0.5 μg '22-oxa'.

EXAMPLE 7

Use of MC 903 lotion in the treatment of acne vulgaris of the face

A total of 10 patients with acne vulgaris of the face have been assessed in an open, non-controlled study of MC 903 lotion. Patients were treated for up to 6 weeks with twice daily applications of the lotion: 50 μg/ml. The study provided evidence that MC 903 lotion was well tolerated. Furthermore, the data pertaining to the therapeutic efficacy of the lotion are encouraging.

The compound designated MC 903 (Example 5 of application No. PCT/DK86/00081) is known as calcipotriol and has the formula:

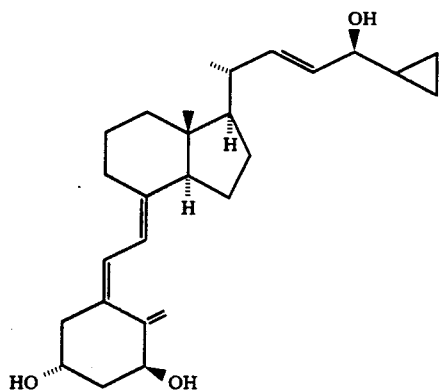
What we claim is:
1. The method of treating acne which comprises administering to a subject in need of such treatment an effective amount of calcipotriol.
2. The method of claim 1 wherein the calcipotriol is administered topically.
* * * * *